United States Patent [19]

Barnett et al.

[11] Patent Number: 4,532,351

[45] Date of Patent: Jul. 30, 1985

[54] PROCESS FOR HYDROGENATING ORGANIC COMPOUNDS BY USE OF GROUP VIII ALUMINUM-SILICATE CATALYSTS

[75] Inventors: Allan E. Barnett; Albert P. Halluin, both of Westfield, N.J.

[73] Assignee: Exxon Research and Engineering Co., Florham Park, N.J.

[21] Appl. No.: 388,966

[22] Filed: Jun. 16, 1982

[51] Int. Cl.$^3$ .................... C07C 85/11; C07C 85/12
[52] U.S. Cl. .................... 564/415; 564/422; 564/423; 564/490; 564/494; 568/881; 568/885; 585/267; 585/269; 585/270; 585/275; 585/276; 585/277; 260/409
[58] Field of Search ............... 585/267, 270, 269, 275, 585/276, 277; 260/409; 564/422, 423, 490, 494, 415; 568/881, 885

[56] References Cited

U.S. PATENT DOCUMENTS

| | | | |
|---|---|---|---|
| 3,320,182 | 5/1967 | Taylor et al. | 252/466 |
| 3,371,050 | 2/1968 | Taylor et al. | 252/459 |
| 3,547,830 | 12/1970 | Shropshire | 252/432 |
| 3,697,445 | 10/1972 | Carter | 252/452 |
| 3,859,370 | 1/1975 | Carter et al. | 260/638 B |
| 3,868,332 | 2/1975 | Carter et al. | 252/452 |
| 3,926,584 | 12/1975 | Adsetts | 218/214 |
| 4,088,603 | 5/1978 | Carter et al. | 252/454 |
| 4,090,980 | 5/1978 | Carter et al. | 252/454 |
| 4,251,394 | 2/1981 | Carter et al. | 252/452 |
| 4,273,680 | 6/1981 | Halluin et al. | 252/466 J |
| 4,273,939 | 6/1981 | Barnett et al. | 564/358 |
| 4,307,248 | 12/1981 | Barnett et al. | 564/358 |
| 4,318,829 | 3/1982 | Halluin et al. | 252/466 J |

*Primary Examiner*—Paul F. Shaver
*Attorney, Agent, or Firm*—Henry E. Naylor

[57] ABSTRACT

Supported catalysts comprised of one or more metals of Group VIII, optionally one or more metals from Group IB and IIA, aluminum and silicate are used for hydrogenating hydrogenatable organic compounds. The catalysts can be produced by coprecipitating metal ions from Group VIII, optionally metal ions from Groups IB and IIA, aluminum ions, and silicate ions, in the presence of solid porous particles.

24 Claims, 4 Drawing Figures

PROCESS FOR HYDROGENATING ORGANIC COMPOUNDS BY USE OF GROUP VIII ALUMINUM-SILICATE CATALYSTS

FIELD OF THE INVENTION

The present invention relates to the hydrogenation of organic compounds by use of novel catalysts comprised of: (a) one or more metals from Group VIII of the Periodic Table of the Elements, (b) solid porous particles, and (c) alumina and silica at a weight ratio of 0.3:1 to 1:0.3 respectively.

BACKGROUND OF THE INVENTION

Coprecipitation of nickel and silicate salts from aqueous solutions in the presence of porous silica or alumina particles to increase the surface area of a catalyst was first disclosed in U.S. Pat. No. 3,371,050 to Taylor and Sinfelt. It was later discovered by J. L. Carter (U.S. Pat. Nos. 3,697,445; 3,859,370 and 3,868,332) that controlled addition of sodium metasilicate in the process of the '050 patent further increases the total surface area of the catalyst as well as the reduced nickel surface area thereby enhancing the catalytic activity of such catalysts. Carter and Barnett (U.S. Pat. No. 4,251,672) later found that the addition of copper salts during coprecipitation enables one to reduce the catalyst at 200° C. rather than at 400° C. and concurrently achieve relatively high hydrogenation activities. Subsequently, Carter, Barnett, and Sinfelt (U.S. Pat. No. 4,263,255) found that by a judicious blend of nickel, cobalt and copper salts during coprecipitation in the presence of sodium metasilicate and kieselguhr, produced a catalyst having extremely high catalytic activities when the catalyst is reduced at 200° C. However, the catalytic activity of such trimetallic catalyst dramatically falls off when the catalyst is reduced at 400° C.

Recently, Halluin and Barnett (U.S. Pat. Nos. 4,273,680 and 4,273,929) discovered that by replacement of the sodium metasilicate in the process of U.S. Pat. No. 3,697,445 with aluminum salts one enhances the catalytic hydrogenation activity of the catalyst. The activity is further enhanced if small amounts of magnesium salts are added during coprecipitation (U.S. Pat. No. 4,307,248 to Barnett and Halluin). Such a pronounced enhancement in activity, however, was not manifested in the catalyst when copper and/or cobalt salts were added during coprecipitation, particularly those metal blend catalysts which were reduced at 200° C.

SUMMARY OF THE INVENTION

In accordance with the present invention there is provided a coprecipitated catalyst support composition as well as novel catalysts resulting therefrom. The catalysts of the present invention are characterized by relatively high activity and stability at elevated temperatures.

The coprecipitated catalyst support composition of the present invention is comprised of: (a) aluminum, one or more salts of aluminum, and one or more oxides of aluminum; (b) silicon, one or more salts of silicon, and one or more oxides of silicon; and (c) solid porous particles.

The support composition of the present invention is prepared by:

(a) preparing an aqueous reaction mixture comprised of (aa) at least one water-soluble aluminum salt, (ab) at least one water-soluble silicate, and (ac) solid porous particles;

(b) heating the aqueous reaction mixture; and (c) adding an alkaline precipitating agent to the heated reaction mixture to coprecipitate aluminum ions and silicate ions in the presence of the solid porous particles.

One method for preparing a catalyst of the present invention is by coprecipitating the aluminum and silicate ions with one or more catalytically active metals during preparation of the support composition. Another method is to impregnate the support composition with one or more catalytically active metals, in a subsequent step.

The catalysts of the present invention may be suitable for such uses as Fisher-Tropsch processes, hydrodesulfurization, and various hydrogenation processes. Of particular interest herein are catalysts suitable for the hydrogenation of organic compounds, preferably olefinic and aromatic compounds. Other hydrogenation reactions for which the catalysts of the present invention may be employed is the hydrogenation of mesityl oxide to MIBK and aldehydes to alcohols.

DETAILED DESCRIPTION OF THE INVENTION

The coprecipitated support compositions and catalysts of the present invention can be prepared by various techniques. For example, all the components of the reaction mixture (e.g., the metal salts and solid porous carrier particles) may be placed in a suitable reaction vessel under acidic conditions and thereafter the hydroxyl ion concentration may be increased while heating and agitating the slurry. In connection with this technique, reference is made to U.S. Pat. No. 4,113,658, the disclosure of which is incorporated herein by reference.

Another technique involves dissolving the metal and aluminum salts (e.g., nickel nitrate and aluminum nitrate) in water with agitation and at elevated temperatures, preferably temperatures ranging from about 60° C. to the solution's boiling point at atmospheric pressure. Higher temperatures may be employed provided the solution is under pressure. The heated metal salt solution is then gradually added to the solid porous particles slurried in an aqueous solution containing silicate salt (e.g. sodium metasilicate). Generally, the dissolved metal ions in the reaction mixture will be kept below about 0.6 mols/liter. This dilution of the dissolved metal ions is one preferred means for obtaining high metal surface area in the catalyst. Preferably, a precipitating agent is added to the heated reaction mixture to aid in the coprecipitation of the metal with the aluminum and silicate ions and porous support particles.

During catalyst preparation, additional water may be added to the reaction mixture to maintain a nearly constant volume so that water loss by evaporation is continually replaced. The aqueous reaction mixture is preferably kept at elevated temperatures, e.g., from about 60° C. to about the boiling point of the solution (at atmospheric pressure) for a period of one to five hours. Heating at a temperature below the boiling point of the solution, i.e., 60°–99° C., may be employed to minimize evaporation. The reaction mixture is then filtered and the resulting product is washed, preferably several times with boiling water, to remove alkali metals ions and other impurities. The product will generally be washed four or more times. The catalyst is then dried at temperatures ranging from about 90°–200° C. for about one to five hours and calcined in an oxygen-containing gas such as air, to a temperature ranging from about 300°–450° C., for a period of about 2–8 hours, preferably about 3–5 hours. The finished catalyst can then be reduced or charged directly (or subsequent to shaping or extruding, such as in the form of tablets or pellets) into a reaction vessel, without activation, and activated in a reaction vessel with a gaseous reductant, usually flowing hydrogen. Alternatively, the catalyst may be prereduced and passivated (stabilized) prior to charging into a reactor.

As previously stated, it is preferred that the catalysts of the present invention be prepared so that coprecipitation is made from dilute solutions. For example, the concentration of catalytically active metal should be no greater than about 1 mol/liter and the concentration of the combination of aluminum salt and silicate should be no greater than about 0.4 mols/liter. The more preferred solution used in preparing the catalysts of the present invention will have: (a) no more than about 0.75 mols/liter of ions of catalytically active metal, most preferably less than about 0.6 mols/liter, and (b) about 0.26 mols/liter of aluminum and silicate ions. Such dilute solutions provide high metal surface area.

The term catalytically active metal as used herein means a metal capable of catalytically transforming, or converting, an organic compound under reaction conditions. Non-limiting examples of catalytically active metals which may be employed in the catalysts of the present invention include those metals selected from the following groups of the Periodic Table of the Elements: Group VIII (Fe, Co, Ni, Ru, Rh, Pd, Os, Ir and Pt); Group IB (Cu, Ag, and Au); Group IIB (Zn, Cd, and Hg); and Group IIA (Be, Mg, Ca, Sr, Ba, and Ra). The Periodic Table of the Elements referred to herein is that table which appears on the inside cover of the 55th Edition (1974–1975) of the *Handbook of Chemistry and Physics,* published by CRC Press.

Non-limiting examples of sources of aluminum ions suitable for use herein are the water-soluble salts of aluminum which includes aluminum nitrate, aluminum sulfate, and aluminum chloride. Preferred is aluminum nitrate.

Non-limiting examples of sources of silicate ions suitable for use herein are the water-soluble silicates. These generally include the alkali metal silicates such as the sodium and potassium silicates, preferably sodium metasilicate. Also suitable is a source of silicic acid ions.

Non-limiting examples of solid porous particles suitable for use herein include alumina, kieselguhr, infusorial earth, diatomaceous earth, siliceous earth, and silica. Preferred is alumina or kieselguhr particles, more preferred is eta and gamma alumina particles, and most preferred is gamma alumina particles.

When nickel and cobalt are employed in the hydrogenation catalysts of the present invention, the weight ratio of nickel to cobalt in the catalyst should range from about 63 to about 0.3, or from about 0.067 to about 0.017.

If a Group IB metal such as copper is employed with nickel and/or cobalt in a hydrogenation catalyst of the present invention, the catalysts should include from about 1 wt. % to about 10 wt. % copper, based on the total weight of the calcined and reduced catalyst.

Up to 10 wt. %, based on the total weight of the calcined and reduced catalyst, of one or more of a Group IIA metal, preferably magnesium or barium, more preferably magnesium, may also be employed. Preferably such a catalyst would be based on nickel, cobalt, or a mixture of nickel and cobalt, and contain about 0.05 wt. % to 10 wt. %, more preferably about 0.1 to 8 wt. %, and most preferably about 0.5 to 6 wt. % of one or more Group IIA metals. Most preferably such a catalyst will be a nickel base catalyst and the Group IIA metal will be magnesium.

The total amount of Group VIII metal in a catalyst of the present invention when the metal is Fe, Co and/or Ni, will generally range from about 10 to about 70 wt. %, based on the total weight of the calcined and reduced catalyst. Preferably about 25 to 60 wt. % of Group VIII metal is present, more preferably about 40 to 55 wt. % of Group VIII metal is present. For catalysts of the present invention based on the platinum Group VIII metals such as platinum, iridium, osmium, palladium, rhodium, and ruthenium, it is preferred, primarily for economic reasons, that the catalyst contain only from about 0.1 to 10 wt. %, preferably 0.15 to 3 wt. % more preferably 0.2 to 2 wt. % of such metals.

The iron, cobalt, and nickel base catalysts of the present invention are preferably prepared by the coprecipitation procedure described herein. Catalysts which are based on catalytically active metals other than iron, cobalt and nickel are preferably prepared by the impregnation procedure described herein.

The weight ratios of $Al_2O_3$ to $SiO_2$ in the calcined catalyst composition derived from the aluminum and silicate slats ranges from about 0.3:1 to 1:0.3, preferably from about 0.4:1 to 1:0.4, and more preferably from about 0.45:1 to 1:0.45. Ideal catalysts of the present invention have been made wherein the ratio is 1:1. Blends outside these ranges have not been shown to provide the benefits of improved catalytic activity and stability as demonstrated by those catalysts of the present invention which are within the above-mentioned ranges.

In the preparation of either the catalyst support composition alone, or the resulting catalyst composition containing one or more catalytically active metals, about 10 to 70 wt. % of the total alumina and/or silica is derived from the solid porous particles - the remainder is derived from precipitated aluminum and silicate ions. Preferably about 30 to 50 wt. % of the total alumina and/or silica content is derived from the solid porous particles.

It is also within the scope of the present invention to employ one or more catalytically active metals with the novel catalyst support composition claimed herein. As previously discussed, these catalytically active metals may be either coprecipitated with the aluminum and silicate ions onto the solid porous particles during preparation of the support composition or they may be impregnated in a subsequent step onto the catalyst support composition by contacting the support composition with an aqueous solution containing ions of one or more catalytically active metals.

In the case of hydrogenation catalysts, it is preferred to coprecipitate the catalytically active metal with the aluminum and silicate ions onto the solid porous particles.

As set forth in the examples to follow, hydrogenation catalysts prepared by use of the novel catalyst support composition of the present invention exhibit relatively low deactivation at elevated temperatures. The consequence of this is that because of the relatively high activity and good heat stability of the catalysts of the present invention, higher throughputs or less total catalyst load to the reactor way be employed to achieve a particular level of activity when compared with hydrogenation catalysts heretofore known.

It is preferred, especially when one or more catalytically active metals are employed, that the coprecipitation of metal ions with aluminum and silicate ions and solid porous particles be completed by the addition of a water soluble alkaline precipitating agent. Alkaline ammonium precipitating agents such as ammonium bicarbonate and ammonia are most suitable for minimizing the amount of alkali metal residue which is removed by washing to avoid poisoning action of the finished catalyst. Although in some instances, alkali precipitating agents may be used where an alkali such as potassium acts as a promoter, rather than a poison. Sodium carbonate is another example of a suitable water-soluble alkali precipitating agent. Various organic alkaline materials such as urea, and primary and secondary amines, may be used to complete the precipitation. However, preferred precipitating agents include ammonium bicarbonate and sodium carbonate.

The precipitated support composition, or catalyst, is preferably washed to remove impurities, particularly sodium. If it is desired to remove trace levels of sodium in the catalyst, one may wash the filter cake with a washing liquor comprised of a mixture of water and a small amount, i.e., about 100 ppm of nitrate, or 200 ppm of ammonium carbonate. In this connection, reference is made to U.S. Pat. No. 4,105,591, the disclosure of which is incorporated herein by reference.

After washing, drying, and calcining, the catalyst can be reduced to activate it. Reduction is carried out in the presence of a reducing gas, preferably hydrogen. The reducing gas is passed over the catalyst at ambient temperature at a rate from about 5 liters/hr/gm to about 30 liters/hr/gm where upon the temperature is raised to a range of from about 75° C. to about 450° C., preferably from about 195° C. to about 400° C.

The copper containing catalysts of the present invention may be reduced at temperatures ranging from about 150° C. to about 250° C., preferably from about 175° C. to about 225° C. The reduction (activation) may be carried out prior to use (and it may be passivated for shipping purposes) or activated after the catalyst has been loaded into the reaction vessel where a reaction such as hydrogenation will be carried out. The reaction vessel may be either batch or continuous. The nature of the reactor will be obvious to one skilled in the art. The activation procedure of U.S. Pat. No. 4,088,603, the disclosure of which is incorporated herein by reference, may be used to activate the catalyst of the present invention.

The activated catalyst is sensitive to deactivation and may not be stored in the presence of oxygen at ordinary temperatures without first being passivated. The passivation step may consist of purging the reactor at a temperature greater than about 150° C. with an inert gas, preferably nitrogen, cooling to ambient temperature, then passing the inert gas over the catalyst while an air bleed is introduced into the inert gas so as to have approximately 1–2 mol percent oxygen present. This procedure will passivate the catalyst by putting a surface oxide coating on it. Preferably, the catalyst will be passivated by the process of U.S. Pat. No. 4,090,980, the disclosure of which is also incorporated herein by reference.

The B.E.T. total surface area of the catalyst of the present invention will generally range from about 150 to about 350 $m^2/g$, preferably from about 255 $m^2/g$ to about 325 $m^2g$. The method for measuring the total catalyst surface area known as the B.E.T. method is described in Emmett, P. H., Advances in Catalysis, I. 65, (1948). Furthermore, the catalyst perferably contains about 0.1 wt. % or less sodium based on the total weight of the catalyst.

Where nickel is chosen as the catalytically active metal herein, the resulting catalyst is capable of having a nickel surface area ranging from about 55 to 100 $m^2/g$ as determined by hydrogen chemisorption after reduction at 400° C., unless otherwise specified, in the manner described by Yates, Taylor and Sinfelt in *J. Am. Chem. Soc.*, 86, 2996 (1964), the disclosure of which is incorporated herein by reference. Furthermore, the catalyst preferably contains about 0.1 wt. % or less of sodium and preferably from about 25 wt. % to about 50 wt. % of nickel based on the total weight of the catalyst.

Where cobalt is chosen as the metal herein, the resulting catalyst is capable of having a cobalt surface area ranging from about 5 to about 20 $m^2/g$ as determined by hydrogen chemisorption (discussed above) after reduction at 400° C. unless otherwise specified. Furthermore, the catalyst preferably contains about 0.1 wt. % or less sodium and preferably from about 25 wt. % to about 60 wt. % of cobalt wherein all weight percents are based on the total weight of the catalyst.

The preferred catalysts of the present invention are particularly useful for hydrogenating hydrogenatable organic compounds. In this connection, the catalysts of the present invention may be used to hydrogenate aromatic containing compounds as typified by: the hydrogenation of benzene to cyclohexane, the hydrogenation of both saturated and unsaturated aldehydes, to alcohols, as in the well-known oxo process; the hydrogenation of double bonds in edible fats and oils, as well as other olefins both straight and branched chain; the hydrogenation of aromatics in white oil base stock to produce high-grade white oil; the hydrogenation of nitro compounds to amines; and the hydrogenation of nitriles to amines. The term, olefins, as used herein, means those unsaturated compounds having at least one multiple bond which includes polyunsaturated compounds as well.

The conditions for the hydrogenation reactions have been discussed very widely and are well known to those skilled in the art. Broadly, the following conditions may be utilized: temperatures ranging from about 250° C. to about 300° C., preferably from about 75° C. to about 25° C.; pressures ranging from about 1 atmosphere to about 800 atmospheres, preferably from about 1 atmosphere to about 50 atmospheres; feed rates from about 0.2 to about 100 volumes per hour per volume of catalyst, and hydrogen addition from about 500 to about 10,000 standard cubic feet per barrel (SCF/B) of feed.

In the case of the oxo process, i.e., the addition of carbon monoxide and hydrogen to alkene to produce alcohols, aldehydes and other oxygenated organic compounds, one would typically employ conditions such that the temperatures would range from about 70° C. to about 175° C. and use a hydrocarbon mole ratio of about 0.5 to about 10 and a pressure of about 100 to about 1000 psig. The alkenes used in such a process would typically contain from 2 to about 20 carbon atoms. The product of such a carbonylation process generally consists, of aldehydes, acetals, unsaturated oxygenated materials and the like, which require hydrofinishing in a second or further hydrogenation stage. It is to the treatment of the aldehyde product, in particular, that the present invention applies. Hydrogenation conditions in this further reaction stage follow those generally employed in the first stage.

Another useful improved hydrogenation is the conversion of aromatics in white oils to yield high quality solvents. Upgrading of white spirits by the process of the instant invention is an improvement in the treatment of such materials.

Still another useful improved hydrogenation of the present invention is the conversion of olefins in paraffin solvents such as denonenizer bottoms and deoctenizer overheads.

Two especially useful hydrogenation processes included within the scope of the invention include the hydrogenation of aromatics such as benzene to cyclohexane and the production of amines from nitro compounds and nitriles. For example, the present invention is useful in converting $C_{12}$ to $C_{24}$ nitriles to the corresponding fatty acid amines. Also, aromatic nitro compounds may be converted to amines, e.g., nitrobenzene to aniline or the conversion of aromatic amines to cycloaliphatic amines, e.g., aniline to cyclohexane amine.

The following examples serve to more fully describe the manner of making and using the above-described invention, as well as set to set forth the best modes contemplated for carrying out various aspects of the invention. It is understood that these examples in no way serve to limit the true scope of this invention, but rather, are presented for illustrative purposes.

Comparative Example

In 460 ml of distilled water there was added 62.9 g $Ni(NO_3)_2.6H_2O$ and 2.8 g of kieselguhr particles. In another 100 ml of distilled water there was dissolved 21.25 g $Na_2SiO_3.9H_2O$. This latter solution was added dropwise over a 15-20 minute period into the first solution as it was being rapidly stirred. The resulting mixture was heated to above 80° C. and 44.4 g $NH_4HCO_3$ was added; the solution was thoroughly mixed for another 30 minutes. The precipitated composition was then filtered and the filter cake was washed four times by reslurrying in one liter of water. The cake was dried at 110° C. and calcined in air for 3 hours at 400° C. A portion of the calcined catalyst was then reduced overnight with hydrogen at 400° C. and used to hydrogenate benzene to cyclohexane. This catalyst is designated Catalyst (A). BET=220 $m^2/g$.

Comparative Example

Catalyst (B) was prepared in accordance with the procedure of the above Comparative Example except 2.8 g of silica was used in place of the 2.8 g of kieselguhr particles. The catalyst had a reduced nickel surface area of 80.4 $m^2/g$.

Comparative Example

Catalyst (C) was prepared in the same manner as Catalyst (A) except that 2.8 g of gamma alumina was used in place of 2.8 g of kieselguhr. The catalyst had a reduced nickel surface area of 72.0 $m^2/g$.

Comparative Example

Catalyst (D) was prepared in the following manner: 62.9 of $Ni(NO_3)_2.6H_2O$ and 33.1 g $Al(NO_3)_3.6H_2O$ was dissolved in 460 ml distilled water. The solution was heated to about 80° C. (which is below the boiling point of the reaction mixture) and 2.8 g of solid porous particles of gamma alumina was added. With rapid stirring, $NH_4HCO_3$ precipitating agent was added as fast as foaming would allow until the dissolved metal was precipitated out of solution. The reaction mixture was maintained at this elevated temperature for 3 hours. The coprecipitated composition was filtered and washed by reslurrying 3 times with 2 liters of hot (>80° C.) distilled water. The resulting filter cake was dried overnight at 110° C. and calcined for 3 hours at 400° C. A portion of the catalyst was reduced overnight in hydrogen at 400° C. The unreduced catalyst had a B.E.T. surface area of 177 $m^2/g$.

EXAMPLE 1

Catalyst (E) was prepared in the following manner: 62.9 g of $Ni(NO_3)_2.6H_2O$, 16.6 g $Al(NO_3)_3.9H_2O$ and 2.8 g kieselguhr were placed in 460 ml of distilled water and rapidly stirred. To this solution there was slowly added 100 ml of an aqueous solution containing 10.6 g of $Na_2SiO_3.9H_2O$. While stirring was continued, the composite solution was heated to about 80° C. under continued agitation and 55 g of $NH_4HCO_3$ was slowly added. The reaction mixture was maintained at 80° C. for 3 hours. The coprecipitated composition was filtered and washed by reslurrying 3 times with 2 liters of hot (>80° C.) distilled water. The resulting filter cake was dried overnight at 110° C. and calcined for 3 hours at 400° C. A portion of the catalyst was reduced overnight in hydrogen at 400° C. The unreduced catalyst had a B.E.T. surface area of 226 $m^2/g$.

A sample of each of Catalysts A, B, C, D and E was used to hydrogenate benzene to cyclohexane. The reaction conditions and results are shown in Table I below.

TABLE I

Catalytic Conversion of Benzene to Cyclohexane[a]

| | Minutes on Stream | | | | |
|---|---|---|---|---|---|
| | 15 | 30 | 60 | 120 | 240 |
| Catalyst A (NiSiO$_2$/kieselguhr) | — | 63% | 61.8% | 57.4% | 57.7% |
| Catalyst B NiSiO$_2$/silica gel) | — | — | 72.0% | — | 69.9% |
| Catalyst C NiSiO$_2$/gamma alumina) | — | — | 86.1% | — | 84.1% |
| Catalyst D (NiAl$_2$O$_3$/kieselguhr) | — | — | 91.4% | 83.7% | 73.2% |
| Catalyst E (NiAl$_2$O$_3$—SiO$_2$/ | 99+% | — | — | — | 98.4% |

TABLE I-continued

| Catalytic Conversion of Benzene to Cyclohexane[a] | | | | | |
|---|---|---|---|---|---|
| | Minutes on Stream | | | | |
| | 15 | 30 | 60 | 120 | 240 |
| kieselguhr) | | | | | |

[a]Reaction Conditions: Pressure: 1 atm; Temperature: 78° C.; Feed: 90% n-hexane, 10% benzene; Feed Rate: 20 cc/hr; $H_2$ rate: 2.4 l/hr.; Catalyst Charge: 0.25 gm (catalyst reduced 16 hr. at 400° C.)

Figure 1:
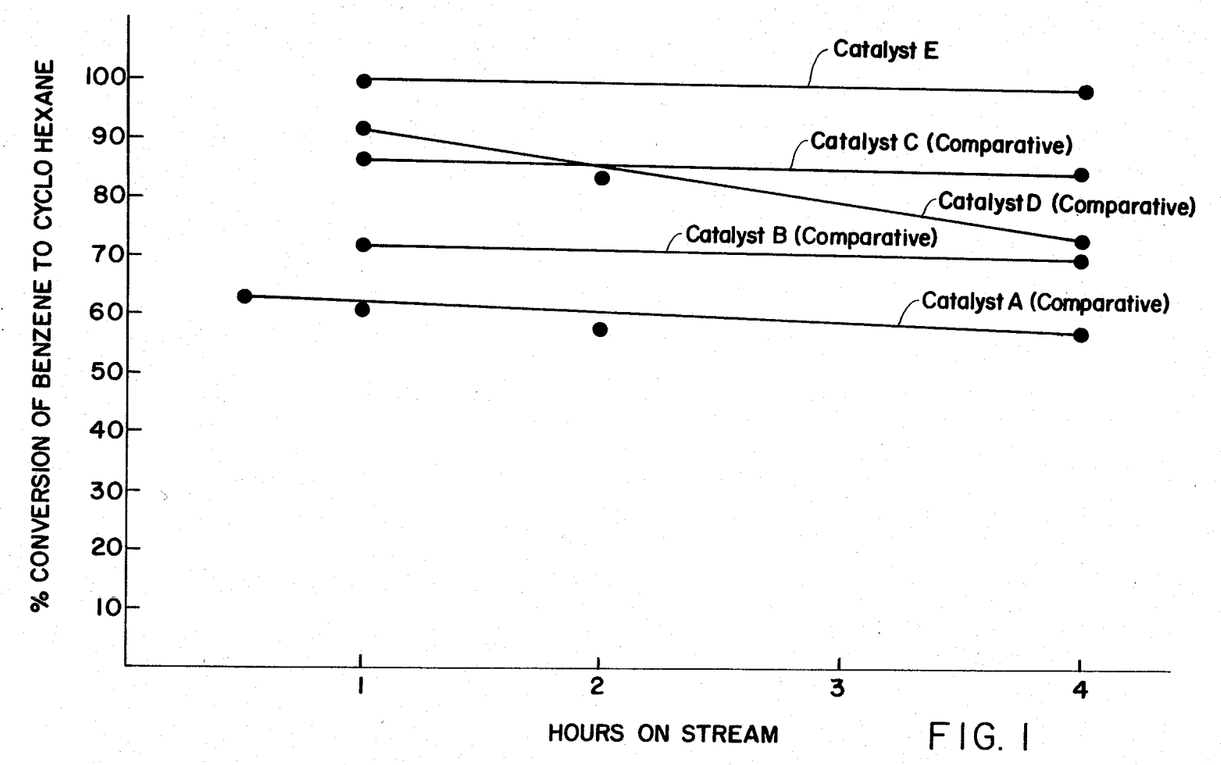
FIG. 1 is a plot of % conversion of benzene to cyclohexane versus time on stream for Comparative Catalysts A, B, C, D, and Catalyst E of the present invention.

The data in Table I illustrates that the mixture of $SiO_2$ and $Al_2O_3$ in the coprecipitated catalyst greatly enhances the hydrogenation activity of the catalyst, particularly when compared to Catalyst A which only contains $NiSiO_2$ and kieselguhr seed. For the purpose of clarity these results are shown in FIG. 1.

Comparative Example

Catalyst (F) was prepared as follows:

62.9 g of $Ni(NO_3)_2.6H_2O$, 33.1 g $(Al(NO_3)_3.6H_2O$ and 3.99 g $Cu(NO_3)_2 3H_2O$ were dissolved in 560 ml of distilled water. The solution was heated to above 80° C. and 2.8 g of solid porous particles of kieselguhr was added. While rapidly stirring, 52.4 g of $NH_4HCO_3$ precipitating agent was added as fast as foaming would allow. The catalyst was washed, dried and calcined as described above. A portion of the catalyst was reduced in hydrogen overnight at 200° C.

EXAMPLE 2

Catalyst (G) was prepared in the following manner:

62.9 g $Ni(NO_3).6H_2O$, 16.6 g $Al(NO_3)_2.9H_2O$, 3.8 g $Cu(NO_3)_2.3H_2O$ and 2.8 g kieselguhr were stirred into 460 ml of distilled water. To this solution there was slowly added 100 ml of an aqueous solution containing 10.6 g $Na_2SiO_3.9H_2O$. 55 g of $NH_4HCO_3$ was slowly added to the stirred reaction mixture. The coprecipitated composition was treated as in Example 5, but a portion of the catalyst was reduced overnight in hydrogen at 200° C. The unreduced catalyst had a B.E.T. surface area of 232 $m^2/g$.

Catalysts F and G were tested for their ability to hydrogenate benzene to cyclohexane. The results are shown in Table II below.

TABLE II

| Catalytic Conversion of Benzene to Cyclohexane[a] | | | | |
|---|---|---|---|---|
| | Minutes on Stream | | | |
| | 15 | 60 | 120 | 240 |
| Catalyst F (Ni—$CuAl_2O_3$/kieselguhr) | 43.3% | — | 37.3% | — |
| Catalyst G (Ni—$CuAl_2O_3SiO_2$/ kieselguhr) | 93.7% | 88.1% | 86.6% | 84.2% |

[a]Reaction Conditions: Pressure: 1 atm; Tempertaure: 78° C.; Feed: 90% n-hexane, 10% benzene; feed rate: 20.0 cc/hr., $H_2$ rate: 20.4 l/hr.; catalyst charge: 0.25 gm (catalyst reduced 16 hr. at 200° C.)

Figure 2:
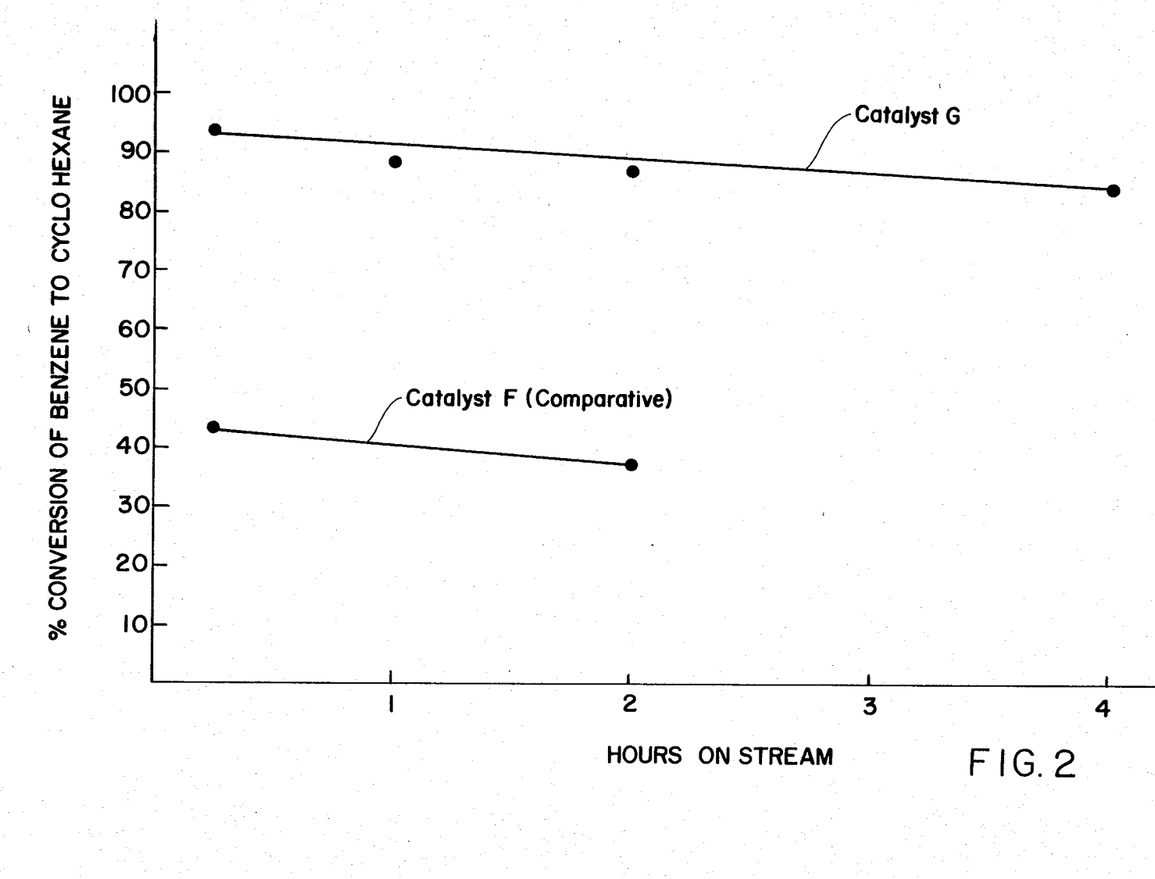
FIG. 2 is a plot of % conversion of benzene to cyclohexane versus time on stream for Comparative Catalysts F and Catalyst G of the present invention.

The data in Table II also illustrate the beneficial effect of the combination of $SiO_2$ and $Al_2O_3$ in the catalyst. These results are surprising since the presence of $Al_2O_3$ alone in the Ni-Cu catalyst systems has less activity than the Ni-Cu-$SiO_2$ catalysts that have been reduced at 200° C. The results of Table II are also shown in FIG. 2 for the sake of clarity.

Comparative Examples

Catalysts (H) and (I) were prepared in the following manner:

To 560 ml of distilled water there was added, with agitation, 56.7 g Ni $(NO_3)_2.6H_2O$, 6.3 g of $Co(NO_3)_2.6H_2O$, 33.1 g $Al(NO_3)_3.9H_2O$ 4.0 g $Cu(NO_3)_2.6H_2O$, and 2.8 g of solid porous particles of kieselguhr. The resulting agitated mixture was heated to above 80° C. (but below the boiling point of the solution) and 69.9 g of $NH_4HCO_3$ was added as fast as foaming would allow. The agitated reaction mixture was maintained at above 80° C. for 3 hours. The coprecipitated composition was filtered and washed by reslurrying 3 times with 2 liters of hot (>80° C.) distilled water. The resulting filter cake was dried overnight at 110° C. and calcined for 3 hours at 400° C. A portion of the catalyst, Catalyst (H), was reduced in hydrogen overnight at 200° C. and another portion, Catalyst (I), was reduced in hydrogen overnight at 400° C.

Comparative Examples

Catalysts (J) and (K) were prepared as follows:

In 2.3 liters of distilled water there was dissolved 267 g $Ni(NO_3)_2.6H_2O$, 32.3 g $Co(NO_3)_2.6H_2O$ and 19.0 g $(Cu(NO_3)_2.3H_2O$, and 14.0 g solid porous particles of kieselguhr particles. A second solution was prepared by dissolving 106.25 g of $Na_2SiO_4.9H_2O$ in 500 ml of distilled water. This second solution was added dropwise into the first solution as it was being rapidly stirred. The resulting mixture was heated to above 80° C. and 212.1 g of $NH_4HCO_3$ was added; the mixture was thoroughly mixed for another 30 minutes. The coprecipitated catalyst composition was then filtered and the filter cake was washed several times by reslurrying with one liter of hot distilled water. The filter cake was dried overnight at 110° C. and calcined for 2 hours at 400° C. A portion of the catalyst, Catalyst (J), was reduced in hydrogen overnight at 200° C. and another portion, Catalyst (K), was reduced in hydrogen overnight at 400° C. Both catalysts (I) and (J), in unreduced form, had a B.E.T. surface area of 246 $m^2/g$.

EXAMPLES 3 AND 4

Catalysts (L) and (M) were prepared as follows:

To 460 ml of distilled water there were added 53.4 g $Ni(NO_3)_2.6H_2O$, 6.5 g $Co(NO_3)_2.6H_2O$, 3.8 g $(Cu(NO_3)_2.3H_2O$, 16.6 g $Al(NO_3)_3.9H_2O$, and 2.8 g of solid porous particles of kieselguhr particles. A second solution was prepared by dissolving 10.6 g of $Na_2SiO_3.9H_2O$ in 100 ml of distilled water. This second solution was added dropwise to the first solution as it was being rapidly stirred. The resulting mixture was heated above 80° C. and 55 g of $NH_4HCO_3$ was added; the mixture was thoroughly mixed for another 30 minutes. The coprecipitated catalyst composition was then filtered and the filter cake was washed several times by reslurrying with one liter of hot distilled water. The filter cake was dried overnight at 110° C. and calcined for 2 hours at 400° C. A portion of the catalyst, Catalyst (L), was reduced in hydrogen overnight at 200° C. and another portion, Catalyst (M) was reduced in hydrogen overnight at 400° C. Both Catalysts (L) and (M) in unreduced form had a B.E.T. surface area of 196 $m^2/g$.

Each of Catalysts H, I, J, K, L and M were tested for their ability to hydrogenate benzene to cyclohexane. The results are shown in Table III below.

TABLE III

| Catalytic Conversion of Benzene to Cyclohexane[a] | | | | |
|---|---|---|---|---|
| | Minutes on Stream | | | |
| | 15 | 60 | 120 | 240 |
| Catalyst H | 40.7% | 39.3% | 39.3% | 33.4% |

TABLE III-continued

Catalytic Conversion of Benzene to Cyclohexane[a]

| | \multicolumn{4}{c}{Minutes on Stream} | | | |
|---|---|---|---|---|
| | 15 | 60 | 120 | 240 |
| Ni—Co—Cu—Al$_2$O$_3$/kieselguhr (Reduced at 200° C.) Catalyst I | 49.3% | 45% | 38.4% | 33.0% |
| Ni—Co—Cu—Al$_2$O$_3$/kieselguhr (Reduced at 400° C.) Catalyst J | 99% | 99% | 99% | 98.3% |
| Ni—Co—Cu—SiO$_2$/kieselguhr (Reduced at 200° C.) Catalyst K | 58% | 47.4% | 53.2% | 45.8% |
| Ni—Co—Cu—SiO$_2$/kieselguhr (Reduced at 400° C.) Catalyst L | 98.4% | 97.7% | 97.7% | 97.2% |
| Ni—Co—Cu—Al$_2$O$_3$—SiO$_2$/kieselguhr (Reduced at 200° C.) Catalyst M | 83% | 72.7% | 69.1% | — |
| Ni—Co—Cu—Al$_2$O$_3$—SiO$_2$/kieselguhr (Reduced at 400° C.) | | | | |

[a]Reaction Conditions: Pressure: 1 atmosphere; Temperature: 78° C.; Feed: 90% n-hexane, 10% benzene; Feed Rate: 20 cc/hr; H$_2$ Rate: 2.4 l/hr., Catalyst Charge: 0.25 g.

Figure 3:
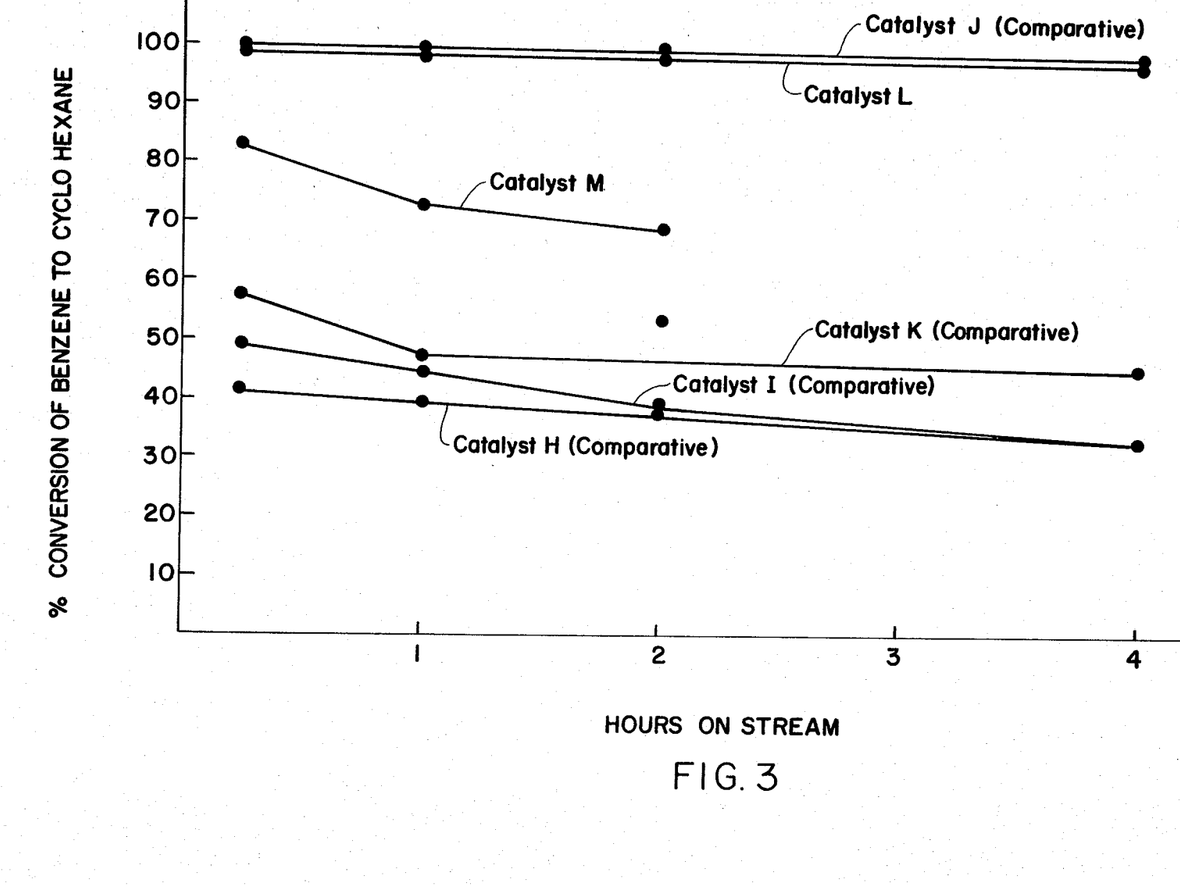
FIG. 3 is a plot of % conversion of benzene to cyclohexane versus time on stream for Comparative Catalysts H, I, J, K, and Catalysts L and M of the present invention.

The data in Table III show that the catalyst of the present invention is comparable to the Ni-Co-Cu-SiO$_2$/kieselguhr catalyst described in U.S. Pat. No. 4,263,225 when reduced at 200° C., except that the catalyst of the present invention (Catalyst M) has a higher activity than Catalyst (K) when reduced at 400° C. Thus, the catalyst of the present invention appears to have a better heat stability. These results are particularly surprising in view of the relatively poor activity shown for the Ni-Co-Cu-Al$_2$O$_3$/kieselguhr Catalysts (H) and (I). For the sake of clarity, these data are graphically shown in FIG. 3.

Comparative Example

To 186 ml of distilled water there was added 74.1 g Ni(NO$_3$)$_2$.6H$_2$O, 21.3 g Al(NO$_3$)$_3$.9H$_2$O, 1.9 g Mg(NO$_3$)$_2$.6H$_2$O, and 1.8 g of solid porous particles of gamma alumina. 60 g of Na$_2$CO$_3$ was dissolved in 200 ml of distilled water this second solution was slowly added to the first solution with rapid agitation. The mixture was heated above 90° C. (but below the boiling point of the solution) and maintained at that temperature for 30 minutes. The resulting coprecipitated catalyst was filtered and washed until the pH of the filtrate had fallen below 8. The filtrate was dried at 110° C. and calcined for 6 hours at 450° C. A portion of the catalyst was reduced in hydrogen overnight at 400° C. The unreduced portion of the catalyst had a B.E.T. surface area of 173 m$^2$/g.

EXAMPLE 5

Catalyst (O) was prepared as follows:
To 400 ml of distilled water there was added 62.9 g Ni(NO$_3$)$_2$.6H$_2$O, 15.6 (Al(NO$_3$)$_3$.9H$_2$O, 1.7 g Mg(NO$_3$)$_2$.6H$_2$O, and 2.8 g solid porous particles of kieselguhr. A second solution was prepared by dissaluing 10.0 g Na$_2$SiO$_3$.9H$_2$O in 200 ml of distilled water. This second solution was added dropwise into the first solution with rapid stirring. The resulting mixture was heated to above 80° C. and 35.0 g of Na$_2$CO$_3$ was added; the mixture was thoroughly mixed for another 30 minutes. The coprecipitated catalyst composition was then filtered and the filter cake was washed several times by reslurrying in one liter of hot distilled water. The filter cake was dried overnight at 110° C. and calcined for 2 hours at 400° C. A portion of the catalyst was reduced in hydrogen overnight at 400° C.

EXAMPLE 6

Catalyst (P) was prepared in the same manner as for Catalyst (N) except that 2.8 g of solid porous particles of gamma alumina seed were used in place of the 2.8 g of kieselguhr.

Each of Catalysts N, O and P were tested for their ability to hydrogenate benzene to cyclohexane. The results are shown in Table IV below.

TABLE IV

Catalytic Conversion of Benzene to Cyclohexane[a]

| | \multicolumn{5}{c}{Minutes on Stream} | | | | |
|---|---|---|---|---|---|
| | 15 | 30 | 60 | 120 | 240 |
| Catalyst N Ni—MgO—Al$_2$O$_3$/gamma alumina | 96.1% | 93% | 85.4% | 78.3% | 72.4% |
| Catalyst O Ni—MgO—Al$_2$O$_3$—SiO$_2$/kieselguhr | 98.1% | — | 96.9% | 96.1% | 95.5% |
| Catalyst P Ni—MgO—Al$_2$O$_3$—SiO$_2$/gamma alumina | 97.0% | — | 94.4% | 93.2% | 93.8% |

[a]Reaction Conditions: Pressure: 1 atmosphere; Temperature: 78° C.; Feed: 90% n-hexane, 10% benzene; Feed Rate: 20 cc/hr; H Rate: 2.4 l/hr., Catalyst Charge: 0.25 g.

Figure 4:
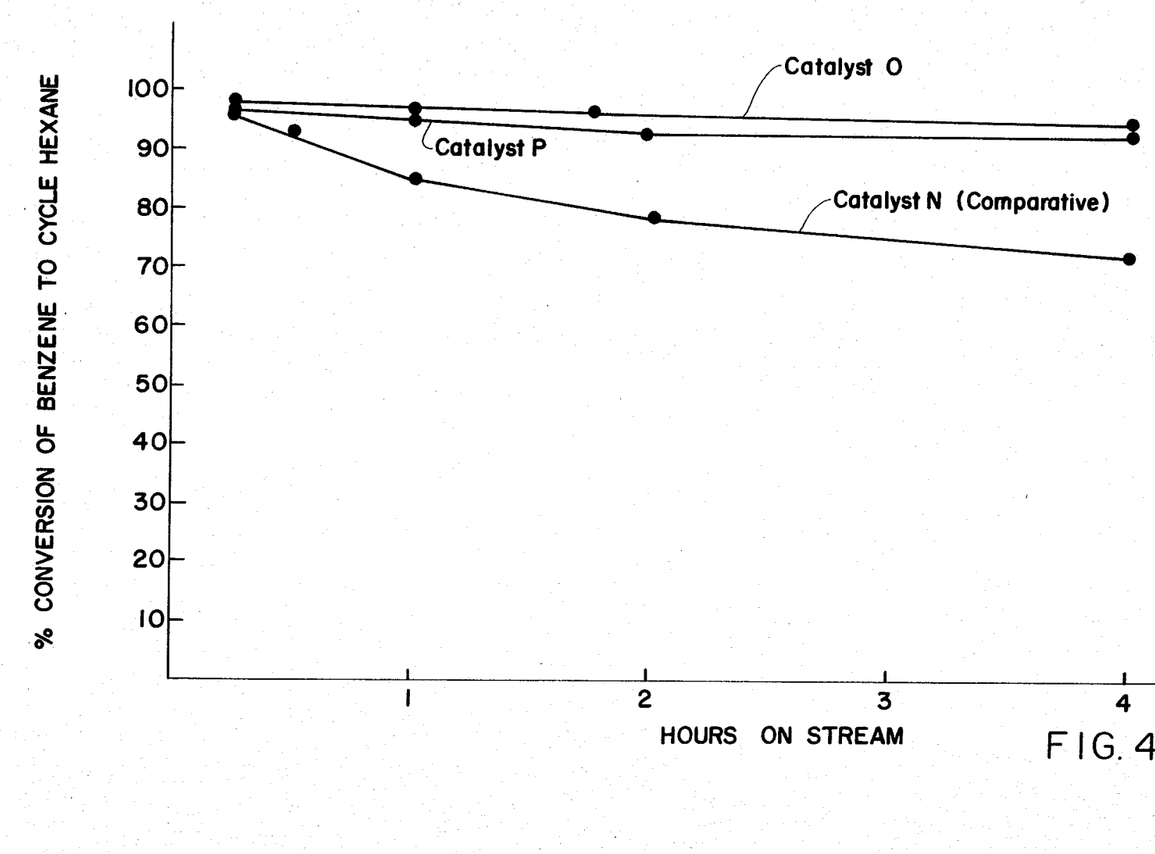
FIG. 4 is a plot of % conversion of benzene to cyclohexane versus time on stream for Comparative Catalysts N, and Catalysts O and P of the present invention.

The data in Table IV further shows the beneficial effect of having both SiO$_2$ and Al$_2$O$_3$ present in the coprecipitated catalyst. The data of Table IV are shown in FIG. 4 for the purpose of clarity.

It is also contemplated herein that the SiO$_2$ derived from the silicate salt can be replaced in whole or in part by metal oxides such as TiO$_2$ derived from titanium salts. In such cases, the weight ratio of Al$_2$O$_3$ to TiO$_2$ would be same as previously specified herein for the Al$_2$O$_3$/5.O$_2$ blends. It is postulated that the coprecipitated and calcined Al$_2$O$_3$ would also have a stabilizing effect on the TiO$_2$ which has a normal tendency to be unstable at elevated temperatures. Such Al$_2$O$_3$/TiO$_2$ systems could provide the support for such catalytic metals as: ruthenium, rhodium palladium, platinum, iridium, osmium in addition to iron, cobalt and nickel.

What is claimed is:

1. A process for hydrogenating organic compounds which process comprises contacting at least one hydrogenatable organic compound with hydrogen in the presence of a supported catalyst comprised of:
   (a) one or more metals from Group VIII of the Periodic Table of the Elements,
   (b) optionally, one or more metals selected from Group IB or IIA of the Periodic Table of the Elements,
   (c) solid porous particles, and
   (d) alumina and silica at a weight ratio of 0.45:1 to 1:0.45 respectively, exclusive of solid porous particles and based on the total weight of the catalyst after calcination,
said catalyst being characterized as having a B.E.T. total surface area ranging from about 150 to about 350 m$^2$/g, wherein the total amount of Group VIII metal in the catalyst ranges from about 10 wt. % to 70 wt. % and the total amount of the Group IB or Group IIA metal in the catalyst is up to 10 wt. %, wherein all weight percents are based on the total weight of the catalyst after calcination and reduction.

2. The process of claim 1 wherein the solid porous particles are selected from the group consisting of alumina, kieselguhr, infusorial earth, diatomaceous earth, siliceous earth, and silica.

3. The process of claim 2 wherein the solid porous particles are alumina or kieselguhr and the precipitating agent is selected from the group consisting of ammonium bicarbonate and sodium carbonate.

4. The process of claim 1 or 3 wherein the Group VIII metal is selected from the group consisting of nickel, cobalt, and mixtures of nickel and cobalt.

5. The process of claim 4 wherein the catalyst contains about 0.1 to 8 wt. % of one or more Group IIA metals.

6. The process of claim 5 wherein the Group IIA metal is magnesium or barium.

7. The process of claim 4 wherein the catalyst contains about 1 to 10 wt. % of one or more Group IB metals.

8. The process of claim 7 wherein the Group IB metal is copper.

9. The process of claim 4 wherein the amount of solid porous particles ranges from about 10 wt. % to about 70 wt. % based on the total amount of alumina and silica in the catalyst.

10. The process of claim 9 wherein the amount of porous particles ranges from about 30 wt. % to about 50 wt. % based on the total amount of alumina and silica in the catalyst.

11. The process of claim 7 wherein the amount of solid porous particles ranges from about 10 wt. % to about 70 wt. % based on the total amount of alumina and silica in the catalyst.

12. The process of claim 11 wherein the amount of solid porous particles ranges from about 30 wt. % to about 50 wt. % based on the total amount of alumina and silica in the catalyst.

13. The process of claim 14 wherein the hydrogenation is conducted at a temperature ranging from about 75° C. to about 300° C., at a pressure ranging from about 1 atmosphere to about 12,000 psig; at a feed rate ranging from about 0.2 to about 100 V/Hr/V and at a hydrogen rate ranging from about 500 to about 10,000 SCF/B.

14. The process of claim 12 wherein the hydrogenation is conducted at a temperature ranging from about 75° C. to about 300° C., at a pressure ranging from about 1 atmosphere to about 12,000 psig; at a feed rate ranging from about 0.2 to about 100 V/Hr/V and at a hydrogen rate ranging from about 500 to about 10,000 SCF/B.

15. The process of claim 1 wherein at least one of the organic compounds is benzene.

16. The process of claim 14 wherein at least one of the organic compounds is benzene.

17. The process of claim 1 wherein at least one of the organic compounds is an aldehyde.

18. The process of claim 14 wherein at least one of the organic compounds is an aldehyde.

19. The process of claim 1 wherein at least one of the organic compounds is a nitrile.

20. The process of claim 14 wherein at least one of the organic compounds is a nitrile.

21. The process of claim 1 wherein at least one of the organic compounds is an olefin.

22. The process of claim 14 wherein at least one of the organic compounds is an olefin.

23. The process of claim 1 wherein the weight ratio of alumina to silica, exclusive of the solid porous particles, is 0.45:1 to 1:0.45.

24. The process of claim 14 wherein the weight ratio of alumina to silica, exclusive of the solid porous particles, is 0.45:1 to 1:0.45.

* * * * *